(12) United States Patent
Campochiaro et al.

(10) Patent No.: US 6,479,729 B1
(45) Date of Patent: Nov. 12, 2002

(54) MOUSE MODEL FOR OCULAR NEOVASCULARIZATION

(75) Inventors: Peter A. Campochiaro, Baltimore, MD (US); Donald J. Zack, Lutherville, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/587,184

(22) Filed: Jun. 5, 2000

Related U.S. Application Data

(63) Continuation of application No. 09/019,704, filed on Feb. 6, 1998, now abandoned.

(51) Int. Cl.[7] .......................... G01N 33/00; A01K 67/00
(52) U.S. Cl. .............................................. 800/18; 800/3
(58) Field of Search ....................................... 800/3, 18

(56) References Cited

U.S. PATENT DOCUMENTS 5,332,671 A    7/1994   Ferrara et al.

OTHER PUBLICATIONS

Mullins et al., Fulminant hypertension in transgenic rats harbouring the mouse Ren–2 gene, 1990, Nature, vol. 344, pp. 541–544.*

Taurog et al., HLA–B27 in inbred and non–inbred transgenic mice: Cell surface expression and recognition as an alloantigen in the absence of human Beta2–microglobulin, 1988, The Journal of Immunology, vol. 141, pp. 4020–4023.*

Hammer et al., Spontaneous inflammatory disease in transgenic rats expressing HLA–B27 and human Beta2m: An animal model of HLA–B27–associated human disorders, 1990, Cell, vol., 63, pp. 1099–1112.*

Mullins et al., Expression of the DBA/2j Ren–2 gene in the adenal gland of transgenic mice, 1989, The EMBO Journal, vol. 8, pp. 4066–4072.*

Tobe et al., Evolution of neovascularization in mice with overexpression in vascular endothelial growth factor in photoreceptors, 1998, Investigative Opthalmology & Visual Science, vol. 39, pp. 180–188.*

Joan W. Miller, "Vascular Endothelia Growth Factor and Ocular Neovascularization" American Journal of Pathology, vol. 151, No. 1, Jul. 1997.

Naoyuki Okamoto et al. "Transgenic Mice with Increased Expression of Vascular Endothelial Growth Factor in the Retina" American Journal of Pathology, vol. 151, No. 1, Jul. 1997.

N. Okamoto et al. "Retinal Neovascularization in Transgenic MICR with Increased Expression of VEGF in the Retina" Investigative Ophthalmology & Visual Science, 1997, vol. 38, No. 4, p. S367.

Wall, Theriogeology, vol. 45, pp. 57–68.

Aszodi et al. J. Molecular Med., vol. 76, pp. 238–252.

Verma eta l. Nature, vol. 389, pp. 239–242.

Zack et al. Neuron, vol. 6, pp. 187–199.

Capecchi, Scientific American, vol. 270 pp. 34–41.

* cited by examiner

Primary Examiner—Michael C. Wilson
(74) Attorney, Agent, or Firm—Banner & Witcoff, Ltd.

(57) ABSTRACT

Transgenic mammals are provided which develop neovascularization of the retina, similar to that found in a variety of disease states, including diabetes, age related macular degeneration, retinopathy of prematurity, sickle cell retinopathy. These mammals can be used as test systems to evaluate potential prophylactic and therapeutic regimens. The effect of a regimen on the neovascularization is indicative of its beneficial effect in a disease state which is associated with neovascularization.

16 Claims, 12 Drawing Sheets

FIG. 7A
FIG. 7B
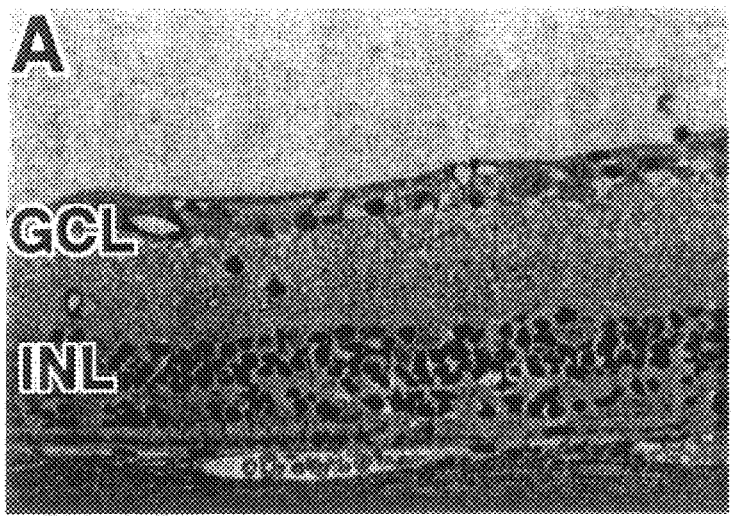
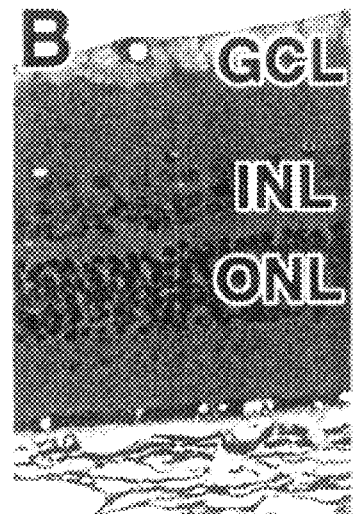

SEQUENCE LISTING

<160> NUMBER OF SEQ ID NOS: 7

<210> SEQ ID NO 1
<211> LENGTH: 2136
<212> TYPE: DNA
<213> ORGANISM: Artificial Sequence
<220> FEATURE:
<223> OTHER INFORMATION: VEGF construct

<400> SEQUENCE: 1

```
aagcttgttg tcagaagcgt tagcgggtaa caagcaaggc catgagtttg agggtcgggg      60
ggacagcctg gccagggcag ggctgcgtgc tctggtcttg acccagggag tccatcgtct     120
gtccctctgt ctggccacca ggggcgtgtt agaatcaaac tcttcacctt gacctcttta     180
gcgatggacc taatcacagg gccaagcacc ttgagcagct gcgccccacc cacccgccac     240
acctgcctgc cccttgctcc ttcccccag agcacttacc accaggctcc ccacacaagt      300
cctgatgctg cccgctgccc gggacagcag ggctctggag cccaggtggg ctgcagcgaa     360
gggagcacgt gtctgagcag agaggtgtag acatcccagg tggtaagagg gacagcacaa     420
gggagcctca gcgatggagg tctcagacac tgggatgctt cctggccacc cttgcgttcc     480
ccacctcggg gcctttgcac tggccgctct ctctccttgg acagctccac cccttagtgc     540
tccttccatc ctcgagttct cagagaggcc ttcctgggcg gctccaggca actgtgtgtc     600
gggaggacgt caccatctga acagtccctg tggtcgtttg tttcatggtt tgtggggcc     660 cctccccgcc ccccagaag aaggacacgt cctacaggca ggggcttggt ccttcttgtc      720
cactgtgtcc cccagaactg agcgtcttgt gtagaacaca gtcggtgcca gataaaactc     780
acagctggac tgtggtcatt gaggaccccg aaggccaggc tgcccgcgac cccacttcac    840
tcctaggagg ggtcttcacg atcctattgt agatgggggc ccttgttcgc accctgagct    900
cgtgctgctg ttctgggata cgccatcacg gcttggcgat cgcacggcac ccgaggccca    960
cggccctaac ccagcctgac cccagtcctg gcctcggccc gtgtgctgtt cccagggccc   1020
accgaaacca tgaactttct gctgtcttgg gtgcattgga gccttgcctt gctgctctac   1080
ctccaccatg ccaagtggtc ccaggctgca cccatgcag aaggaggagg gcagaatcat   1140
cacgaagtgg tgaagttcat ggatgtctat cagcgcagct actgccatcc aatcgagacc   1200
ctggtggaca tcttccagga gtaccctgat gagatcgagt acatcttcaa gccatcctgt   1260
gtgcccctga tgcgatgcgg gggctgctgc aatgacgagg gcctggagtg tgtgcccact   1320
gaggagtcca acatcaccat gcagattatg cggatcaaac ctcaccaagg ccagcacata   1380
ggagagatga gcttcctaca gcacaacaaa tgtgaatgca gaccaaagaa agatagagca   1440
agacaagaaa atcctgtgg gccttgctca gagcggagaa agcatttgtt tgtacaagat   1500
```

-continued

```
ccgcagacgt gtaaatgttc ctgcaaaaac acagactcgc gttgcaaggc gaggcagctt    1560
gagttaaacg aacgtacttg cagatgtgac aagccgaggc ggtgagccag ataccgatgc    1620
tgccgcagca aaagcaggag cagatgccgc cgtcgcaggc gaagatgtcg cagacggagg    1680
aggcgatgct gccggcggag gaggcgaagt aagtagaggg ctgggctggg ctgtgggggg    1740
tgtggggtgc gggacttggg catgtctggg agtccctctc accactttttc ttacctttct    1800 aggatgctgc cgtcgccgcc gctcatacac cataaggtgt aaaaaatact agatgcacag    1860
aatagcaagt ccatcaaaac tcctgcgtga aatttttacc agacttcaag agcatctcgc    1920
cacatcttga aaaatgccac cgtccgatga aaaacaggag cctgctaagg aacaatgcca    1980
cctgtcaata aatgttgaaa actcatccca ttcctgcctc ttggtccttg ggcttgggga    2040
ggggtgcgcg gatgtggtta gggaacatga ctggtcaaat gggaagggct tcaaaagaat    2100
tcccaatatt gactaccaag ccacctgtac agatct                              2136
```

<210> SEQ ID NO 2
<211> LENGTH: 18
<212> TYPE: DNA
<213> ORGANISM: Artificial Sequence
<220> FEATURE:
<223> OTHER INFORMATION: PCR primer

<400> SEQUENCE: 2
tccagccgga gccccgtg                                                    18

<210> SEQ ID NO 3
<211> LENGTH: 18
<212> TYPE: DNA
<213> ORGANISM: Artificial Sequence
<220> FEATURE:
<223> OTHER INFORMATION: PCR primer

<400> SEQUENCE: 3
gcagcagccc ccgcatcg                                                    18

<210> SEQ ID NO 4
<211> LENGTH: 20
<212> TYPE: DNA
<213> ORGANISM: Artificial Sequence
<220> FEATURE:
<223> OTHER INFORMATION: PCR primer

<400> SEQUENCE: 4
tgcagatgtg acaagccgag                                                  20

<210> SEQ ID NO 5
<211> LENGTH: 30
<212> TYPE: DNA
<213> ORGANISM: Artificial Sequence
<220> FEATURE:
<223> OTHER INFORMATION: PCR primer

<400> SEQUENCE: 5
gatgtggcga gatgctcttg aagtctggta                                       30

<210> SEQ ID NO 6
<211> LENGTH: 20
<212> TYPE: DNA
<213> ORGANISM: Artificial Sequence
<220> FEATURE:
<223> OTHER INFORMATION: PCR primer

<400> SEQUENCE: 6

```
cactgcaaac ggggaaatgg                                              20

<210> SEQ ID NO 7
<211> LENGTH: 20
<212> TYPE: DNA
<213> ORGANISM: Artificial Sequence
<220> FEATURE:
<223> OTHER INFORMATION: PCR primer

<400> SEQUENCE: 7
tgagatggac tgtcggatgg                                              20
```

MOUSE MODEL FOR OCULAR NEOVASCULARIZATION

This is a continuation of Application Ser. No. 09/019,704, filed Feb. 6, 1998, now abandoned.

This invention was supported using funds from the U.S. Public Health Service. Particularly, grants EY05951, EY10017, EY09769, and core grant P30EY1765. The U.S. government therefore retains some rights in the invention.

TECHNICAL FIELD OF THE INVENTION

This invention is related to the field of retinopathies, particularly those caused by neovascularization.

BACKGROUND OF THE INVENTION

New blood vessel formation or neovascularization (NV) is essential for normal eye development, but it can also cause severe ocular disease. In the retina, NV is associated with a number of disease processes, the most common of which is diabetic retinopathy, a major cause of new blindness in developed nations[1]. Occlusion of retinal vessels leading to retinal ischemia is a feature shared by most diseases in which retinal NV occurs. This observation led to the hypothesis that the development of retinal NV is stimulated by one or more angiogenesis factors released by ischemic retina[2, 3]. Substantial effort has been devoted to identifying the factor or factors involved.

The demonstration that vascular endothelial cell growth factor (VEGF) is upregulated by hypoxia[4, 5] and that levels of VEGF are increased in the retina and vitreous of patients[6-9] or laboratory animals[10, 11] with ischemic retinopathies has focused attention on VEGF as a potential mediator of retinal angiogenesis. This is supported by studies showing that VEGF antagonists partially inhibit retinal or iris NV in animal models[12-14]. There is also ample data indicating that VEGF can stimulate NV in other tissues[15-18].

Despite this evidence associating VEGF with retinal NV, there is conflicting data as to whether VEGF alone is sufficient to induce retinal NV. There are patients with nonproliferative diabetic retinopathy or other retinal diseases who have elevated levels of retinal VEGF, yet no evidence of retinal NV[19-20]. In primates, multiple intravitreous injections of VEGF result in iris NV[21] and retinal vascular abnormalities including endothelial cell proliferation[23], but do not cause definite retinal NV. Similarly, implantation of VEGF sustained release pellets into the vitreous of primates[23] or into the subretinal space of rats[34] falls to stimulate retinal NV. In rabbits; however, transient retinal NV occurs after intravitreous implantation of VEGF sustained release pellets[23].

The basis for these conflicting data concerning the effects of VEGF in the retina compared to other tissues is unclear, but possible contributing factors may be differences in retinal vessels compared to those in other vascular beds, differences in the vascular microenvironment, such as higher levels of angiogenesis inhibitors in the retina, or difficulty in maintaining a sufficiently high level of exogenously administered VEGF in the retina. There are tight junctions between vascular endothelial cells of retina and brain, but not those of most other organs. Glia of retina and brain induce barrier characteristics to microvessels[25], and may also act to inhibit retinal NV[26]. There are also differences between retinal and brain microvessels, with the former having a greater amount of pericyte coverage[27] and pericytes have been demonstrated to inhibit endothelial cell proliferation[28]. These differences are important because the vascular microenvironment modulates the effects of angiogenic stimuli[29], and therefore their effects in one vascular bed may not be predictive of their effects in another.

There is a continuing need in the art for new tools to study neovascularization and ways and means to treat and prevent this major cause of blindness.

SUMMARY OF THE INVENTION

It is an object of the present invention to provide a transgenic mammal useful for studying neovascularization of the retina.

It is another object of the present invention to provide a transgenic mouse useful for developing medicinal, radiological, and gene therapies for neovascularization.

It is an object of the present invention to provide a method for screening compounds for use in treating and preventing retinopathies.

Another object of the invention is to provide a method for screening radiological and gene therapies for use in treating and preventing retinopathies.

These and other objects of the invention are achieved by providing a transgenic mammal comprising a polynucleotide encoding VEGF under the transcriptional control of a retina-specific promoter. The mammal expresses VEGF in the retina.

According to another aspect of the invention a transgenic mouse is provided. The mouse comprises a polynucleotide encoding human VEGF under the transcriptional control of a rhodopsin promoter. The mammal expresses VEGF in the retina. Intraretinal and subretinal neovascularization develops.

Another embodiment of the invention provides a method of screening test compounds as potential drugs for preventing and treating neovascularization lesions. A test compound is administered to a transgenic mammal which comprises a polynucleotide encoding VEGF under the transcriptional control of a retina-specific promoter. The mammal expresses VEGF in the retina The number or area of neovascularization lesions in the retina of the transgenic mammal is determined. A test compound which prevents or reduces the number or area of neovascularization lesions is a potential drug for preventing or treating neovascularization lesions, such as occur in disease states, including diabetes, age related macular degeneration, retinopathy of prematurity, sickle cell retinopathy.

In yet another embodiment of the invention a method of screening test therapies as potential therapies for preventing and treating neovascularization lesions is provided. A transgenic mammal is subjected to a test therapy. The mammal comprises a polynucleotide encoding VEGF under the transcriptional control of a retina-specific promoter. The mammal expresses VEGF in the retina. The number or area of neovascularization lesions in the retina of the transgenic mammal is determined. A test therapy which prevents or reduces the number or area of neovascularization lesions is a potential therapy for preventing or treating neovascularization lesions.

The present invention thus provides the art with an extremely useful model of retinal and subretinal neovascularization. The model is relatively cheap and reliable, does not require any exogenous agent, and has many characteristics of clinical intraocular neovascularization.

The oligonucleotide primers used to screen genomic DNA for presence of the transgene are represented by P1 and P2. The primers used for RT-PCR are represented by P3 and P4. The transcription start site is marked +1.

Figure 2:
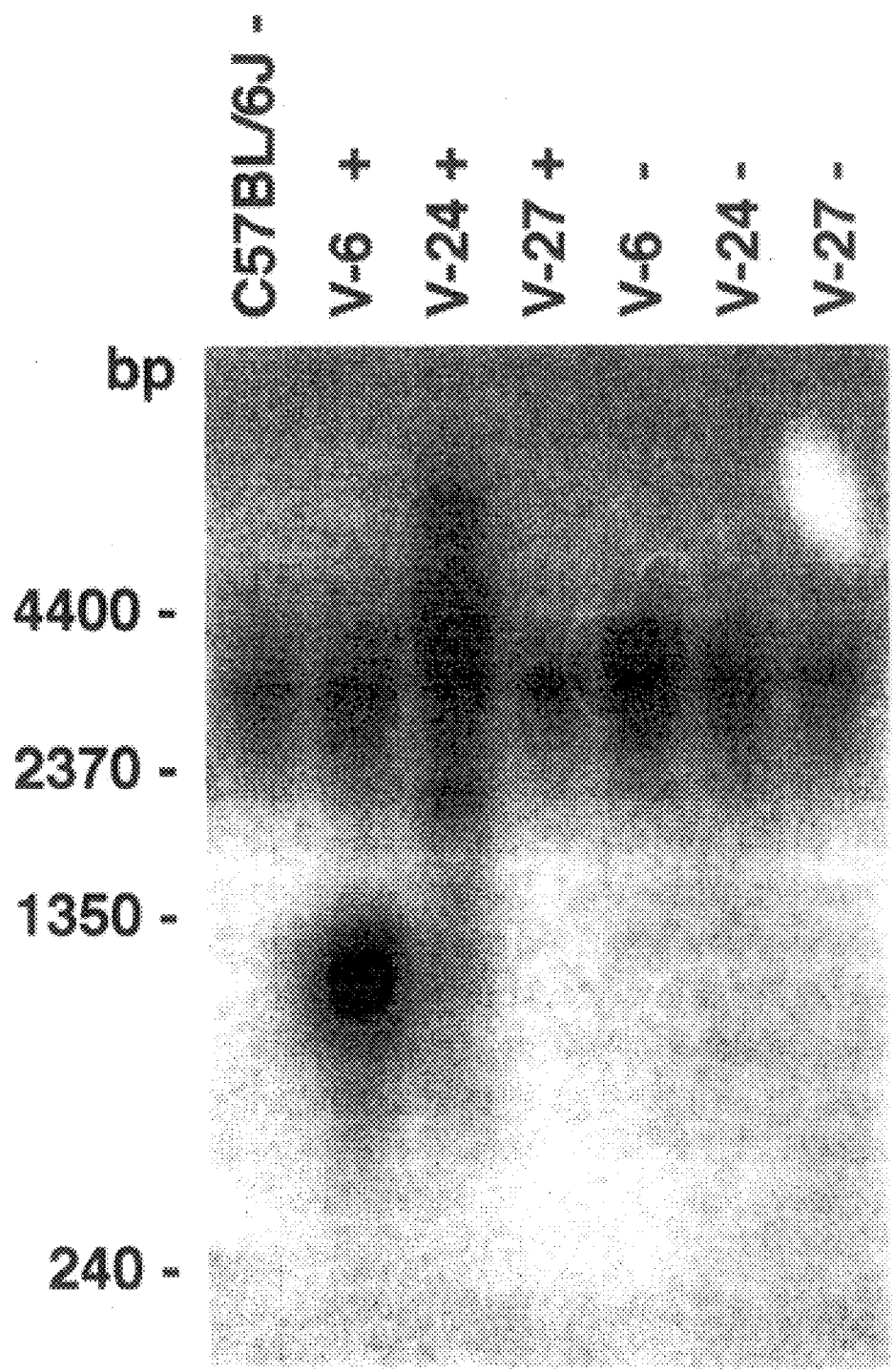

FIG. 2. Assessment of VEGF mRNA in retinal RNA by Northern analysis.

Total RNA was isolated from the retinas of several 3 month old transgene-positive (+) or transgene-negative (−) mice from each line (V-6, V-24, and V-27) or from control mice (C57BL/6J) and 10 µg for each was loaded in the designated lane. Northern hybridization was done with a $^{32}$P-labeled BamHl fragment of hVEGF. A prominent 1.0 kb band, the predicted size for VEGF transgene mRNA, is seen only in the lane containing retinal RNA from V-6+ mice, although a faint band is present in the V-24+ lane. All of the lanes contain a band ranging from 3.3 to 4.0 kb which encompasses the sizes of several previously reported VEGF transcripts in mouse tissue and therefore likely represents endogenous VEGF mRNA.

Figure 3A:
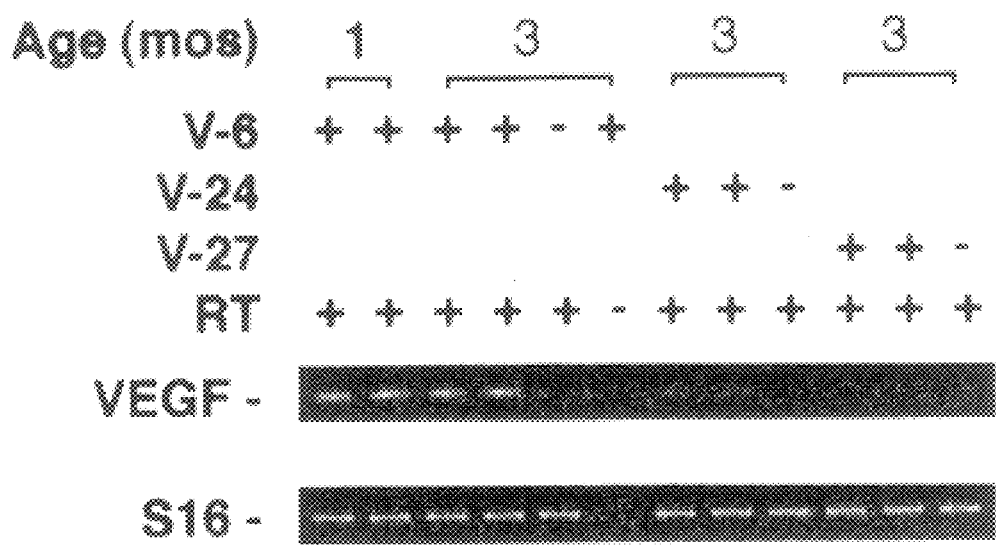
Figure 3B:
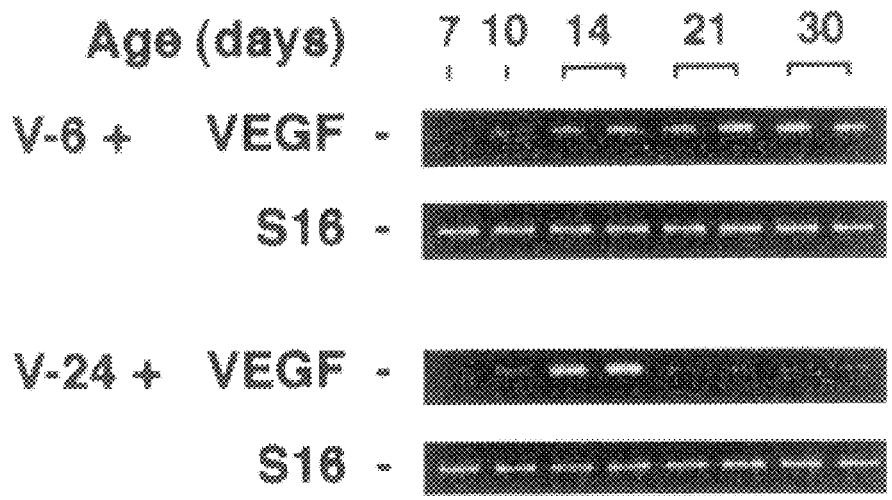

FIGS. 3A–3B. Assessment of transgene mRNA level in retinal RNA by RT-PCR.

Total RNA was extracted from the retina of transgene-positive (+) or negative (−) V-6, V-24, or V-27 mice and RT-PCR was done simultaneously for VEGF transgene mRNA and S16 ribosomal protein mRNA. The size of the band amplified with transgene primers was compatible with the 293 bp predicted for amplification from mRNA and was absent (as was the band for S16) when reverse transcriptase (RT) was excluded from the reaction (FIG. 3A). Only retinas from V-6+ mice show a good signal for VEGF transgene mRNA at 3 months after birth (FIG. 3B). A signal is barely detectable in 7 day old V-6+ mice (not reproduced well in this figure), but is easily seen in 10 day-old or older mice. Transgene mRNA is detected at 7 days in V-24+ mice and a strong signal is seen at 14 days and then decreases as photoreceptor degeneration occurs.

FIGS. 4A–4E. Immunohistochemical staining for VEGF in the retina of V-6+ and control mice.

Frozen sections of retina from three 3 month old V-6+ mice (FIGS. 4A, 4C, and 4E) and a 3 month old V-6− mouse (FIG. 4B) were immunohistochemically stained using an affinity-purified anti-hVEGF antibody. Reaction product (AEC, red) is seen in photoreceptors in transgene-positive mice (arrows, FIGS. 4A, 4C, and 4E), but not the transgene-negative mouse (FIG. 4B). Expression was focal which is typical of the rhodopsin promoter that was used; in FIG. 4C there is staining overlying an area of NV, while adjacent photoreceptors are negative (arrowheads). x175. In (FIG. 4D), preabsorption of primary antibody with antigenic peptide almost completely abolished staining on a section adjacent to the one shown in (FIG. 4C). x175. (FIG. 4E) Higher magnification in a transgene-positive mouse shows red reaction product easily discernible in photoreceptor inner and outer segments. Arrows point to the outer limiting membrane which is present between inner segments and the outer nuclear layer. x500.

FIGS. 5A–5H. Intraretinal and subretinal NV in V-6+ mice.

FIGS. 5A–D. Serial sections through an area of fluorescein leakage in a 1 month old V-6+ mouse shows 2 areas (large arrows on left and thin arrows on right) in which new vessels extend from the deep capillary bed in the inner nuclear layer, through the outer nuclear layer, to the outer segment layer of the photoreceptors, where they are partially surrounded by proliferated retinal pigmented epithelial (RPE) cells (arrowheads). This is unequivocal NV, because blood vessels are not normally seen in the outer retina.

Figure 5A:
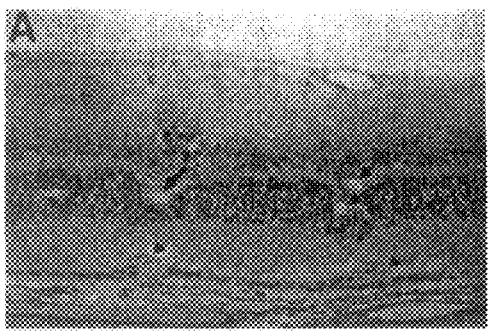
Figure 5B:
Figure 5C:
Figure 5D:
Figure 5E:
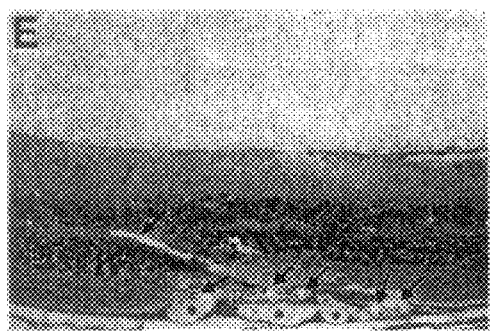

FIG. 5E. A 3 month old V-6+ mouse shows a large vessel extending from the inner nuclear layer, through the outer nuclear layer (uppermost arrow) to a plexus of blood vessels among photoreceptor outer segments (lower arrows), a region that is referred to as the subretinal space. The blood vessels are partially surrounded by RPE cells, some of which contain large cavities (asterisks).

Figure 5F:
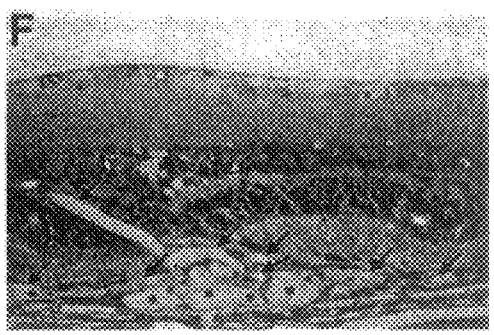

FIG. 5F. A 4 month old V-6+ mouse shows a very similar area of retinal NV as that seen in the 3 months-old mouse in (E). There is a large vessel extending from the inner nuclear layer through the outer nuclear layer (uppermost arrow) into the subretinal space where many blood vessel lumens (lower arrows) are partially or completely surrounded by RPE, some of which contain cavities (asterisks).

Figure 5G:

FIG. 5G. Higher magnification of an area shown in [C] allows resolution of endothelial cell nuclei (arrows) lining the lumen (asterisks) of one blood vessel that is turning or two adjacent blood vessels passing through the outer nuclear layer.

Figure 5H:
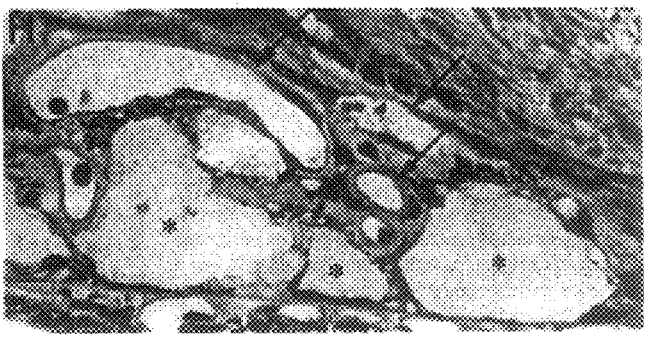

FIG. 5H. High magnification of the region of the subretinal space shown in (F) allows easy distinction between the numerous lumens of new blood vessels (arrows) and cavities within RPE cells (asterisks).

Figure 6:
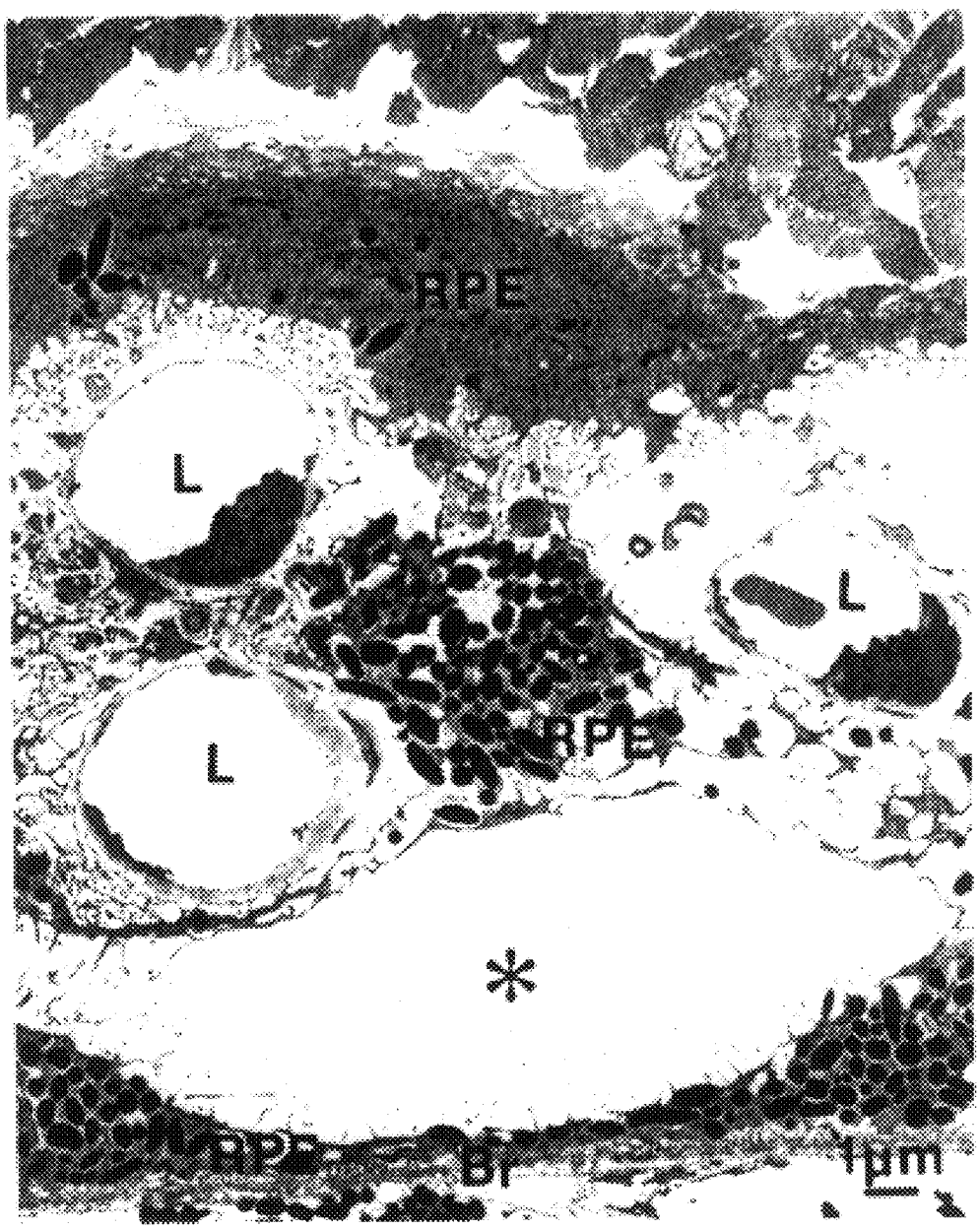

FIG. 6. Electron microscopy of subretinal neovascularization in a 3 month old V-6+ mouse.

Electron microscopy of the same area shown in FIG. 5E shows 3 lumens (L) of the neovascular complex with an underlying retinal pigmented epithelial cell (RPE) resting on Bruch's membrane (Br). There is a large cavity (asterisk) within the RPE cell.

FIGS. 7A–7B. Retinal degeneration in V-24+ mice.

FIG. 7A. The retina of a 3 month old V-24+ mouse shows marked loss of photoreceptor cells, that have cell bodies that make up the outer nuclear layer (ONL). There is some disorganization of the inner nuclear layer (INL), which is typical of severe photoreceptor degenerations. The ganglion-cell layer (GCL) is normal.

FIG. 7B. The retina of a control C57BL/16J mouse showing normal ONL, INL, and GCL for comparison.

Figures 8A, 8B:
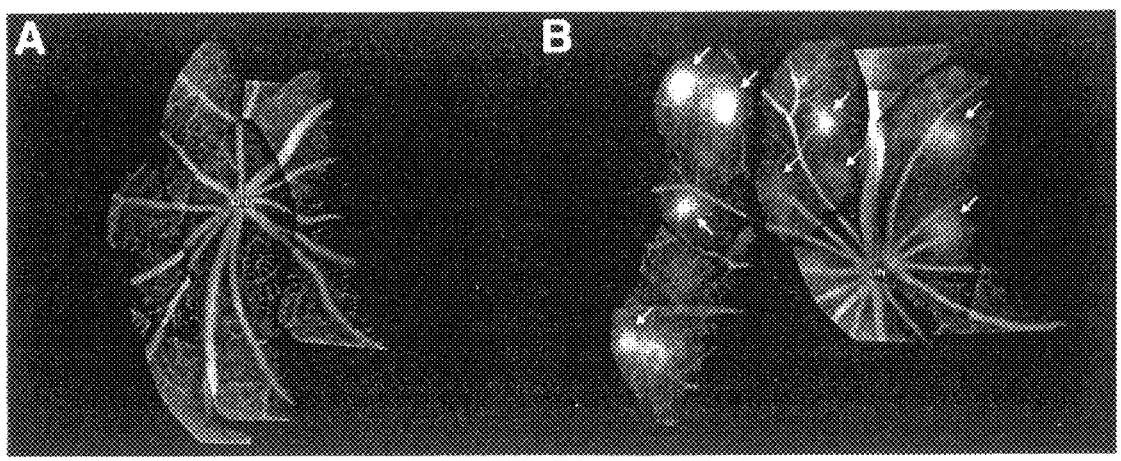

FIGS. 8A–8B. Fluorescein angiography in 3 month old V-27+ and V-6+ mice.

The V-27+ mouse (FIG. 8A) has a normal-appearing retinal vasculature. The central retinal artery enters at the optic nerve (ON) and divides into several branches that radiate out in all directions. Small discreet blood vessels are seen between the major vessels. Fluorescent dye is confined within blood vessels, because of tight junctions between normal retinal vascular endothelial cells. The V-6+ mouse (FIG. 8B) has numerous hyperfluorescent spots with fry boarders throughout the retina (arrows), indicating areas of fluorescein leakage. Histopathologic evaluation of these areas demonstrates subretinal NV (see FIG. 6). The dye leaks out because the new vessels lack tight junctions between endothelial cells.

FIG. 9A–9F. Evolution of morphological changes in the retina after the onset of VEGF expression in photoreceptors.

Figure 9A:
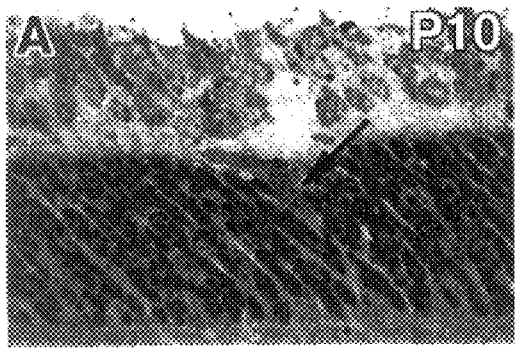

FIG. 9A. On postnatal day 10 (P10), ectopic cells were identified at the inner border of the outer nuclear layer (arrow).

Figure 9B:
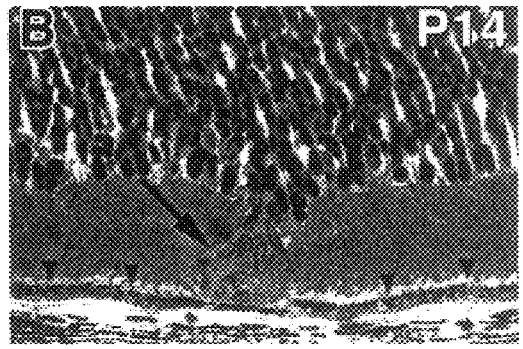

FIG. 9B. Cells (arrow) similar to those seen in (A) are located among photoreceptor inner and outer segments adjacent to the RPE (arrowheads) on P14.

Figure 9C:
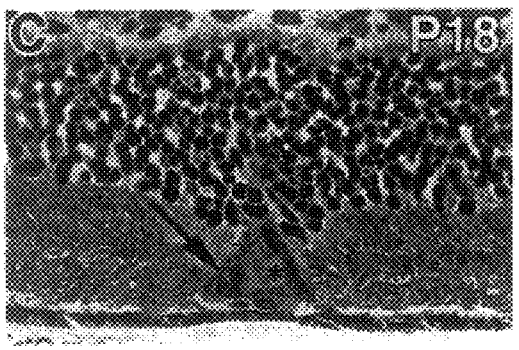

FIG. 9C. An aggregate of cells among photoreceptors (arrow) on P18 has an erythrocyte within a lumen (asterisk), indicating that it is organized into a perfused blood vessel.

Figure 9D:
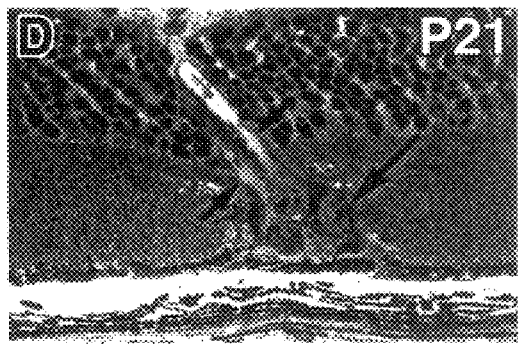

FIG. 9D. A well formed blood vessel with two lumens (small arrows) is seen extending through the outer nuclear layer to a clump of cells among photoreceptor inner and outer segments (large arrow) on P21.

Figure 9E:

FIG. 9E. On P31, a blood vessel with a large lumen (asterisk) is seen in the subretinal space and is partially covered by RPE cells (arrowheads).

Figure 9F:
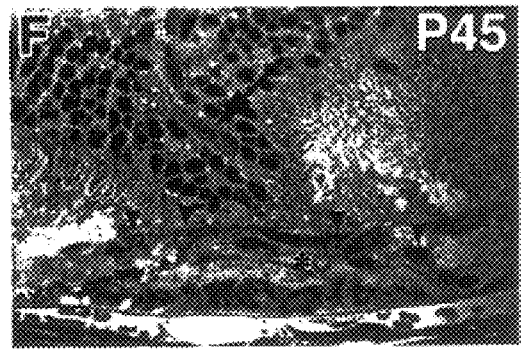

FIG. 9F. A vessel wall in the outer nuclear layer (large arrow) extends to a large plexus of vessels in the subretinal space on P45. An erytirocyte is seen in a lumen adjacent to the asterisk and RPE cells (arrowheads) cover much of the vascular complex.

FIG. 10A–10E. Ultrastructural features of newly forming blood vessels in rhodopsin/VEGF transgenic mice.

Figure 10A:
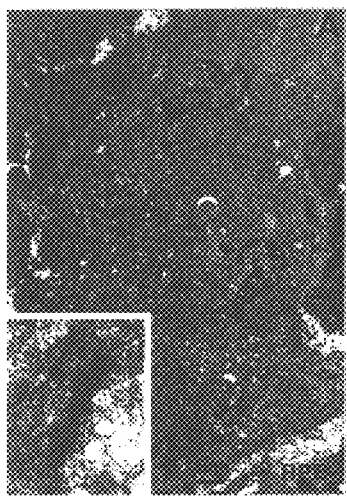

FIG. 10A. The cells located among photoreceptor outer segments (OS) adjacent to the RPE on P14 shown in FIG. 2B have an undifferentiated appearance and lack pigment. There are tight junctions between some of the cells, which are shown within the rectangle and at higher magnification in the inset.

Figure 10B:

FIG. 10B. Cells located among OS on P18, shown in FIG. 2C, have numerous intercellar tight junctions (arrowheads) and form a lumen (L) containing erythrocytes.

Figure 10C:
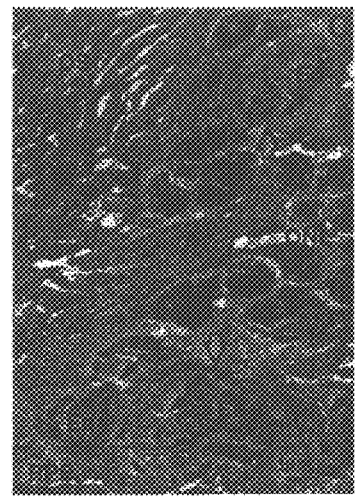

FIG. 10C. Endothelial cells (En) of newly formed vessels (large open arrows) located adjacent to the RPE and among OS on P21, as shown in FIG. 2D, have numerous tight junctions (arrowheads) and slit-like lumens between them (small black arrows).

Figure 10D:
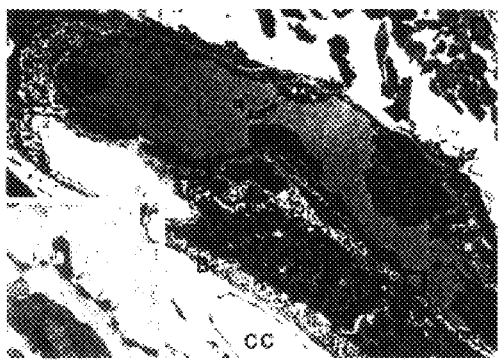

FIG. 10D. The blood vessel in the subretinal space on P31 shown in FIG. 2E has a large lumen (L) formed by thin-walled endothelial cells (En) that have many fenestrations (inset). The vessel has pericytes (P) and is partially surrounded by RPE. Bruch's membrane (Br) is intact and the choriocapillaris (CC) appears normal.

Figure 10E:
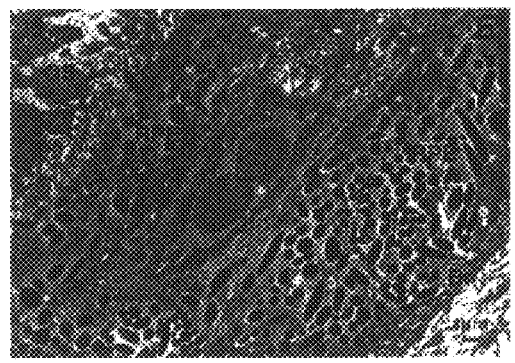

FIG. 10E. A new blood vessel (large arrow) in the subretinal space on P45, shown in FIG. 2F, is completely surrounded by RPE cells. The endothelial cells have thick walls and no fenestrations, unlike the endothelial cells shown in FIG. 11D.

Figure 11A:
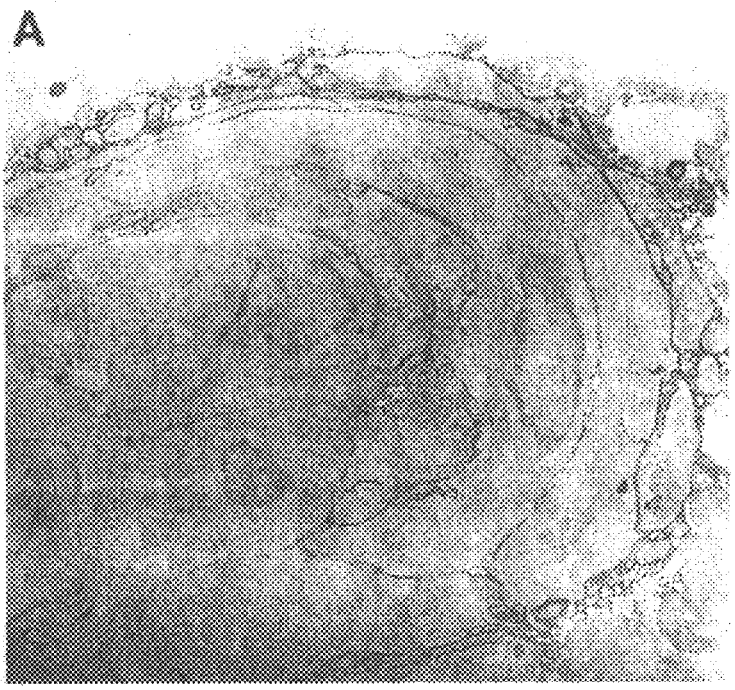
Figure 11B:

FIG. 11A–11B. Electron microscopic immunocytochemical staining of ectopic cells in the outer retina with an endothelial cell marker, Griffonia simplicifolia isolectin $B_4$.

FIG. 11A. A clump of ectopic cells among photoreceptor outer segments shows reaction product coating their surface membranes.

FIG. 11B. The same area shown in (A) counterstained with uranyl acetate to show the ultrastructure of the ectopic cells.

FIG. 12A–12H. Retinal whole-mounts in rhodopsin/VEGF transgenic mice perfused with fluorescein-labeled dextran FIG. 12A. Normal retinal vasculature in a transgene-negative P21 mouse.

Figure 12A:
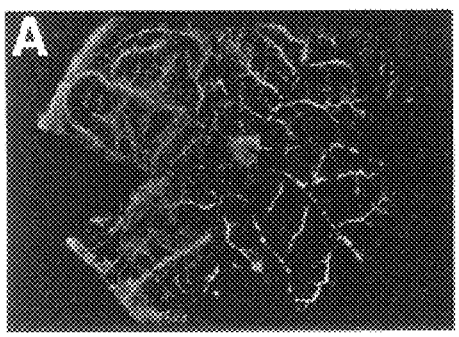
Figure 12B:
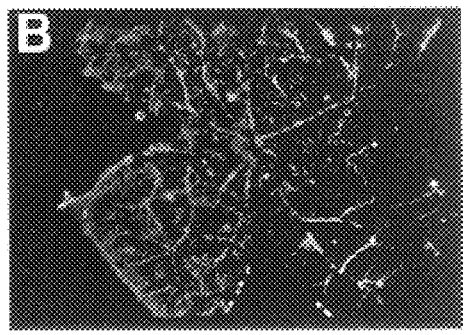

FIG. 12B. At low power, it is difficult to resolve NV in a P21 transgene-positive mouse.

Figure 12C:
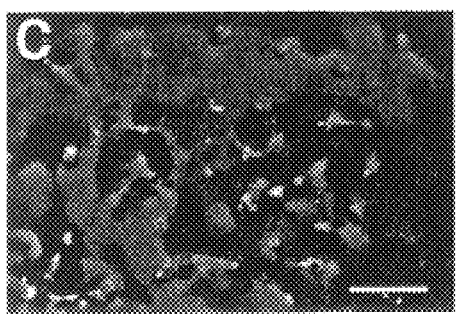

FIG. 12C. At higher power, the retina from (B) shows numerous tufts of NV at the level of the outer segments. Retinal vessels are out-of-focus in the background. Bar is 100 m.

Figure 12D:
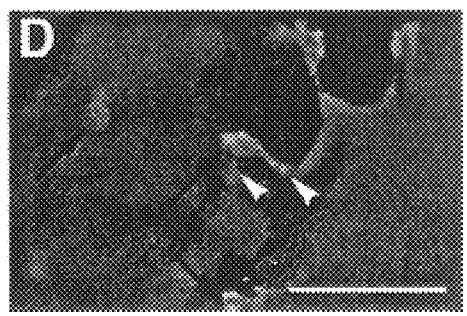

FIG. 12D. At even higher power, small vessels (white arrowheads) are seen connecting the tufts of NV (arrows) to retinal vessels.

Clumps of RPE cells (black arrowheads) are located adjacent to many of the tufts. Bar is 100 m.

Figure 12E:
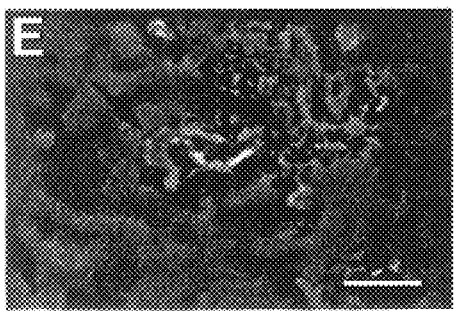

FIG. 12E. A P31 mouse shows a fairly large frond of NV with associated RPE on the photoreceptor side of the retina. Bar is 100 m.

Figure 12F:
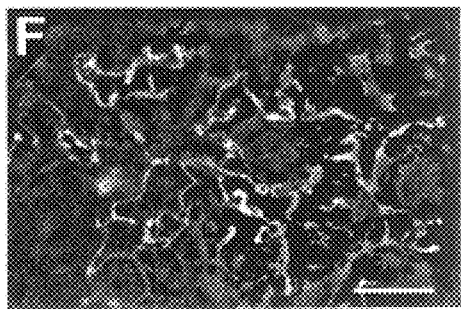

FIG. 12F. Large loops of NV with associated RPE are seen on the photoreceptor side of the retina in a 6 week old transgene-positive mouse. Bar is 100 m.

Figure 12G:
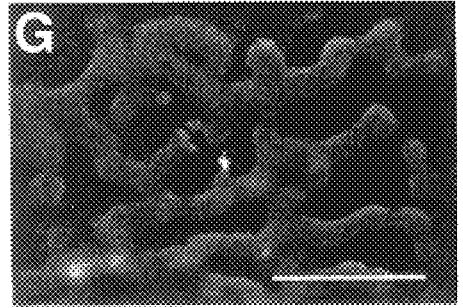

FIG. 12G. A small twig of NV is seen sprouting from a retinal vessel in the deep capillary bed of a P14 transgenic mouse. Bar is 100 m.

Figure 12H:
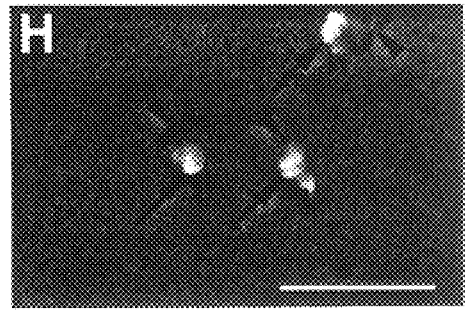

FIG. 12H. Small buds of NV (arrows) have reached the photoreceptor layer in a P18 mouse. RPE (arrowheads) is associated with the NV. Bar is 100 m.

DETAILED DESCRIPTION

It is a discovery of the present inventors that transgenic mammals can be made which develop neovascularization in the retina. These animals provide a useful model for studying retinal diseases, as well as for identifying useful regimens for treating or preventing the diseases. The mammals contain a polynucleotide encoding VEGF under the transcriptional control of a retina-specific promoter. The mammals express VEGF in the retina above a baseline amount for normal, non-transgenic mammals. Moreover, the mammals develop neovascularization spontaneously in the course of their development.

Mammals according to the present invention include without limitation rodents, such as rats and mice, dogs, cats, pigs, sheep, cows, goats, and horses and rabbits. Desirably the mammal is non-human. Transgenic animals are those which have incorporated a foreign gene into their genome. A transgene is a foreign gene or recombinant nucleic acid construct which has been incorporated into a transgenic animal. The transgene may be a wild-type or mutant gene, or one which has been altered to express in an aberrant pattern. Briefly, transgenic animals are made by injecting egg cells with a nucleic acid construct according to the present invention. The injected egg cells are then implanted into the uterus of a female for normal fetal development. Animals which develop which carry the transgene are then backcrossed to create heterozygotes for the transgene. Methods for making transgenic animals are well known in the art. See, e.g., Watson, J. D., et al., "The Introduction of Foreign Genes Into Mice," in Recombinant DNA, 2d Ed., W. H. Freeman & Co., New York (1992), pp. 255–272; Gordon, J. W., Intl. Rev. Cytol. 115:171–229 (1989); Jaenisch, R., Science 240: 1468–1474 (1989); Rossant, J., Neuron 2: 323–334 (1990).

The recombinant DNA molecules of the invention may be introduced into the genome of mammals using any method for generating transgenic animals known in the art. Embryonal target cells at various developmental stages are used to introduce the transgenes of the invention. Different methods are used depending on the stage of development of the embryonal target cell(s). These include, without limitation: 1. Microinjection of zygotes; Brinster, et al., Proc. Natl. Acad. Sci. (USA) 82: 4438–4442 (1985); 2. Viral integration; Jaenich, R, Proc. Natl. Sci. (USA) 73: 1260–1264; Jahner, et al., Proc. Natl. Acad. Sci. (USA) 82: 6927–6931 (1985); Van der Putten, et al., Proc. Natl. Acad. Sci. (USA) 82: 6148–6152 (1985); 3. Embryonal stem (ES) cells obtained from pre-implantation embryos that are cultured in vitro. Evans, M J., et al., Nature 292: 154156 (1981), Bradley, M. O., et al., Nature 309: 255–258 (1984); Gossler, et al., Proc. Natl. Acad. Sci. (USA) 83:9065–9069 (1986); Robertson et al., Nature 322: 445448 (1986).

In one particular method, production of transgenic mice employs the following steps. Male and female mice, from a defined inbred genetic background, are mated. The female is sacrificed and the fertilized eggs are removed from her uterine tubes. At this time, the pronuclei have not yet fused and it is possible to visualize them in the light microscope. Foreign DNA or the recombinant construct is then microinjected (100–1000 molecules per egg) into a pronucleus. Shortly thereafter fusion of the pronuclei (a female pronucleus and a male pronucleus) occurs and, in some cases, foreign DNA inserts into (usually) one chromosome of the fertilized egg or zygote. The zygote is then implanted into a pseudo-pregnant female mouse (previously mated with a vasectomized male). The embryo develops for the full gestation period. The surrogate mother delivers the potentially transgenic mice. The newborn mice are tested for the presence of the foreign or recombinant DNA. Conveniently, a portion of the tail (a dispensable organ) is removed and the DNA extracted. DNA-DNA hybridization (in a dot blot, slot blot or Southern blot test) can be employed to determine whether the mice carry the foreign or recombinant DNA. Of the eggs injected, on average 10% develop properly and produce mice. Of the mice born, on average one in four (25%) are transgenic for an overall efficiency of 2.5%. Once these mice are bred they transmit the foreign gene in a normal (Mendelian) fashion linked to a mouse chromosome.

The constructs which are useful according to the present invention are those which will lead to tissue-specific expression of VEGF. Typically this will be due to the genetic linkage to transcriptional control elements which are activated in a particular tissue or cell type. The present invention is particularly concerned with promoters which cause increased expression of VEGF in the retina or in particular cells of the retina, such as the retinal pigmented epithelium (RPE) or the photoreceptor cells. The expression need not be exclusively in the retina. For example, promoters which are activated in the RPE as compared to other tissues may be used, even though their expression is not solely found in the retina. Suitable promoters for use in the present invention include the rhodopsin promoter, the opsin promoter, the IRBP promoter, neuron specific enolase promoter, the tyrosinase-related protein-1 promoter. See, e.g., Raymond S M *Current Biology*, 5:1286–1295 (1995) and Lowings, *Mol. Cell Biology* 12:3653–3662 (1992), and Jackson, *Nucleic Acids Research* 19:3799–3804 (1991). Other suitable promoters can be found by looking for differentially displayed genes in libraries of retinally expressed or retinal pigmented epithelium-expressed genes. Thus promoters which are expressed at least 10-fold more in the retina or RPE as compared to another reference tissue, such as the liver or heart may be used in the present invention.

The VEGF coding sequence which is used may be derived from any species, including but not limited to human and bovine VEGF. The VEGF encoding polynucleotide may, for example, be obtained from rats, mice, dogs, cats, pigs, sheep, cows, goats, horses, and rabbits. Wild-type or mutant, whether naturally-occurring or synthetic, may be used. The polynucleotide may encode the signal sequence of VEGF or it may have the signal sequence deleted. See, e.g., Ferrarra U.S. Pat. No. 5,332,671, which provides the sequences for both bovine and human VEGF.

The mice which are particularly useful for the present invention are those in which neovascularization develops in the retina. The neovascularization may be, for example, in the retina, in the subretinal space, or in the choroid. As a preliminary matter, potentially transgenic mice are screened to ensure the presence of the transgene. Secondarily, retinas of transgenic mice can be screened to ensure that the VEGF is being expressed. This can be done by any means known in the art, including Northern blot, RT-PCR, immunohistochemistry, Western blot. Any technique which is convenient can be used. Neovascularization can be tested, for example, by 10 using light microscopy, immunostaining, electron microscopy. Retinas can be flat mounted or whole mounted, as is desired.

The neovascularizing transgenic mice of the present invention can be used to screen regimens for prevention and treatment of neovascularization. Thus if regimens are provided before the neovascularization develops, such as is before postal day 6 in mice, and neovascularization is delayed or prevented, then a prophylactic regimen has been identified. If the regimen is administered after neovascularization has developed, and the regimen causes a reduction, cessation, or regression, then a therapeutic regimen has been identified. The regimen may be administration of a test compound or other medicinal chemistry or natural products sample. The regimen may also be application of a dye and laser or administration of a foreign gene. Even surgical techniques can be tested on the transgenic animal model of the present invention.

The above disclosure generally describes the present invention. A more complete understanding can be obtained by reference to the following specific examples which are provided herein for purposes of illustration only, and are not intended to limit the scope of the invention.

EXAMPLE 1

Generation of Transgenic Animals

A full length cDNA for human VEGF was cloned into a plasmid containing the 2.2 kb HindIII/NaeI fragment from the bovine rhodopsin promoter[30]. The plasmid also contained an intron and a polyA addition site derived from the mouse protamine gene and a eukaryotic consensus ribosomal binding site. After transformation, a clone with correct orientation was selected. DNA was double CsCl purified and cut with EcoRI to provide a 3341 bp fusion gene FIG. 1). The fusion gene was purified and transgenic mice were generated using established techniques as previously described[30].

Figure 1:
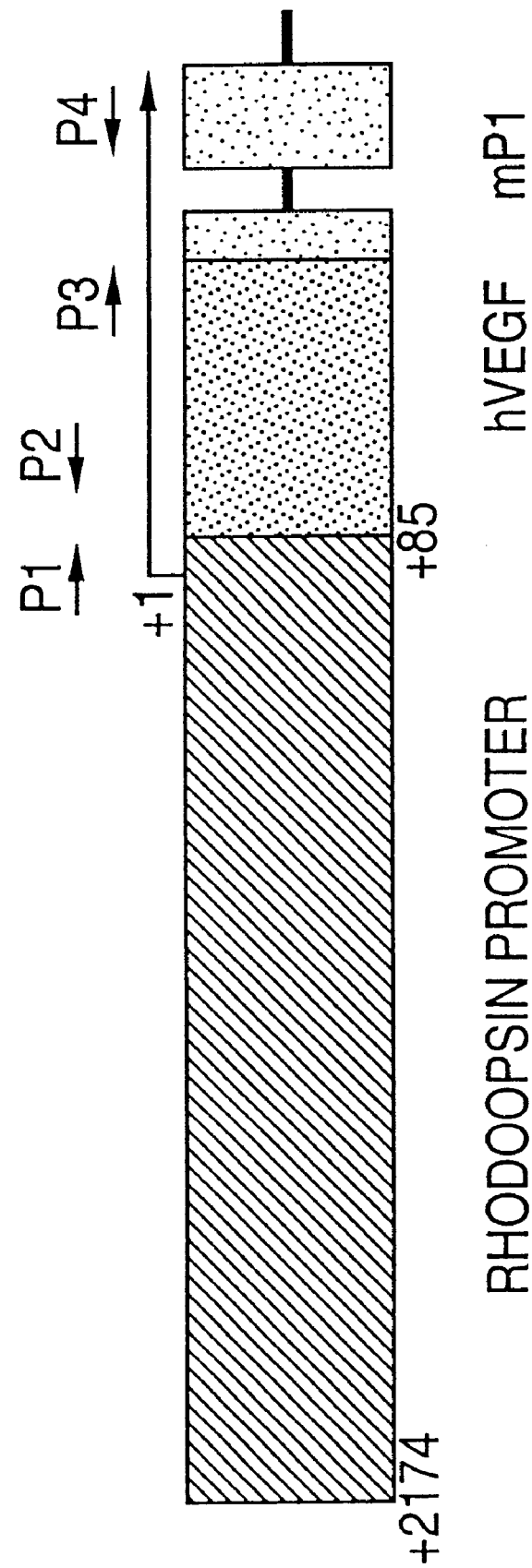
FIG. 1. Schematic map of the rhodopsin/VEGF fusion gene.

Mice were screened for the presence of the transgene by either Southern blot analysis or by polymerase chain reaction (PCR) of tail DNA[30]. Tail pieces were digested overnight at 55° C. in 50 mM Tris (pH 7.5), 100 mM EDTA, 400 mM NaCl, 0.5% SDS containing 0.6 g/l proteinase K. For PCR at 58° C., two 18 bp primers, P1 (5'-TCCAGCCGGAGCCCCGTG-3'; SEQ ID NO:2) and P2 (5'-GCAGCAGCCCCCGCATCG-3'; SEQ ID NO:3) were chosen so as to amplify 337 bp of transgene-specific sequence (FIG. 1).

Three independent lines that incorporated the rhodopsin promoter/VEGF fusion gene (FIG. 1) were obtained (designated V-6, V-24, and V-27). The founders were backcrossed with C57BL/6J mice to establish transgenic lines. As determined by Southern blot analysis, the transgene copy numbers for lines V-6, V-24, and V-27 were 3–4, 13–15, and 2–3, respectively. Mice that were heterozygous at the transgene locus were used in all analyses.

EXAMPLE 2

Fluorescein Angiography of Transgenic Mice

Fluorescein angiography provides a means to visualize the retinal vasculature in vivo and assess vascular permeability, which is increased in new vessels.

Mice were anesthetized by brief placement in a beaker containing gauze moistened with ether followed by intraperitoneal injection of 120 g/g body weight of ketamine hydrochloride (Fort Dodge, Iowa) and pupils were dilated with 1% tropicamide drops. Mice were given an intraperitoneal injection of 12 l/g body weight of 1% fluorescein sodium (Alcon, Fort Worth, Tex.) and after 1 minute, fundus photographs were taken of all four quadrants of the retina with a Topcon TRC-50FT fundus camera (Topcon, Tokyo, Japan) using a 495 nm excitation filter and a 570 nm barrier filter and Tmax 400 black and white film (Kodak, Rochester, N.Y.).

Fluorescein angiography was done on several mice from each line at 2 weeks, 1 month, and 3–4 months after birth. No leakage occurred in any of the 2 week old mice or any of the V-27+ mice at any age (FIG. 7A). At 1, 3, and 4 months of age, V-6+ mice showed multiple discrete leakage spots scattered throughout the retina (FIG. 7B). Abnormal fluorescence was seen in 1 and 3 month old V-24+ mice due to retinal degeneration (not shown).

EXAMPLE 3

Measurement of Transgene mRNA Expression by RT-PCR

The time course of retinal VEGF transgene expression was assessed by semi-quantitative reverse transcription coupled to polymerase chain reaction (RT-PCR). At appropriate time points, mice were sacrificed, eyes were removed, and retinas were dissected. Retinal RNA was isolated using the guanidine isothiocyanate method as described by Chomczynski and Sacchi[31]. Reverse transcription was carried out with 0.5 µg of total RNA, reverse transcriptase (SuperScript II, Life Technologies, Gaithersburg, Md.), and 5.0 M oligo d(T) primer. Aliquots of the cDNAs were used for PCR amplification with primers for the hVEGF/mP1 fusion gene that amplify across an intron-exon border, P3 (5'-TGCAGATGTGACAAGCCGAG-3'; SEQ ID NO:4) and P4 (5'-GATGTGGCGAGATGCTCTTGAAGTCTGGTA-3'; SEQ ID NO:5) (FIG. 1). The expected PCR products for the hVEGF/mP1 fusion gene fragment from genomic DNA and mRNA are 364 bp and 270 bp, respectively. Titrations were performed to insure that PCR reactions were carried out in the linear range of amplification. Mouse S16 ribosomal protein primers (5'-CACTGCAAACGGGGAAATGG-3' (SEQ ID NO:6) and 5'-TGAGATGGACTGTCGGATGG-3' (SEQ ID NO:7)) were used to provide an internal control for the amount of template in the PCR reactions.

At 1 and 3 months of age, V-6+ mice showed detectable expression of the VEGF transgene in the retina (FIG. 3A). There appeared to be little difference in level of expression between different mice at the same time point or between 1, 2, 3, and 4 month old mice (2 and 4 month old data not shown). Three month old V-24+ mice showed only a faint signal and no signal was detectable in RNA from retinas of V-27+ mice. The expression at early time points was examined in retinas of V-6+ mice; there was a faint signal at 7 days (not well reproduced in FIG. 3B) that increased through 21 days and then appeared relatively constant thereafter FIG. 3B). Retinal degeneration occurs in V-24+ mice (see below), and therefore we sought to determine if there is very high expression of the transgene prior to the degeneration. A modest signal was seen at 7 days, was relatively strong at 14 days, and then decreased thereafter FIG. 3B).

EXAMPLE 4

Measurement of Transgene mRNA by Northern Analysis

RNA blot hybridization analysis was done as previously described[32] using 10 µg of total retinal RNA. The cDNA probe was the 598 bp BamHI fragment of hVEGF labeled with $^{32}$P by hexanucleotide random priming. Hybridization temperature was 42° C. The membrane was washed twice for 30 minutes at 60° C. in 1×SSC, 0.2% SDS, followed by two washes of 30 minutes each at 65° C. in 0.2×SSC, 0.2% SDS.

Retinal expression of the VEGF transgene in 3 month old animals was assessed by Northern analysis. For each fine, RNA from the retinas of transgene-positive mice, or from transgene-negative littermates, was pooled and analyzed. RNA from the retinas of transgene-positive V-6 (V-6+) mice showed a strong signal at 1.0 kb, the predicted size for the VEGF fusion gene transcript (FIG. 2). V-24+ retinas demonstrated a faint band at 1.0 kb. In contrast, retinal RNA from V-27+ mice, all transgene-negative littermates, and control C57BL/6J mice, all failed to show any detectable 1.0 kb signal. The 3.3–4.0 kb band observed in all lanes is the same size as that previously demonstrated in Northerns for VEGF in mouse embryos[33] and presumably represents endogenous VEGF mRNA.

EXAMPLE 5

Expression of VEGF Protein in Transgenic Mouse Retinas

At 3 months after birth, transgenic and littermate control mice were sacrificed, their eyes were removed, fixed in 4% paraformaldehyde, and embedded in paraffin. Ten m sections were cut and immunohistochemically stained as previously described[30, 32] with a 1:500 dilution of rabbit anti-hVEGF antibody (Santa Cruz Biotechnology, Inc., Santa Cruz, Calif.). Specificity of stag was assessed by substitution of nonimmune serum for primary antibody and by preabsorption of primary antibody with antigenic peptide.

Figure 4A:
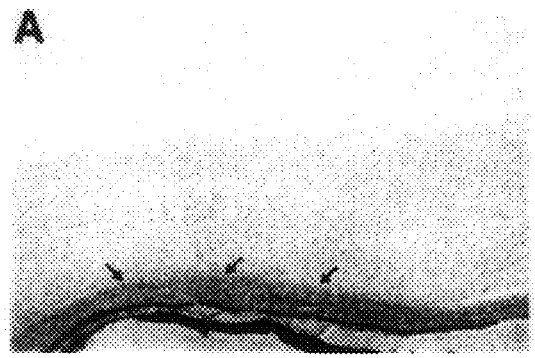
Figure 4B:
Figure 4C:
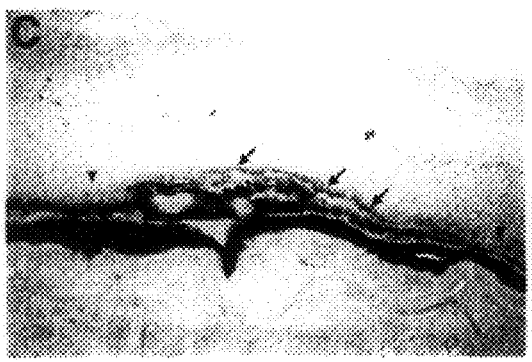
Figure 4D:
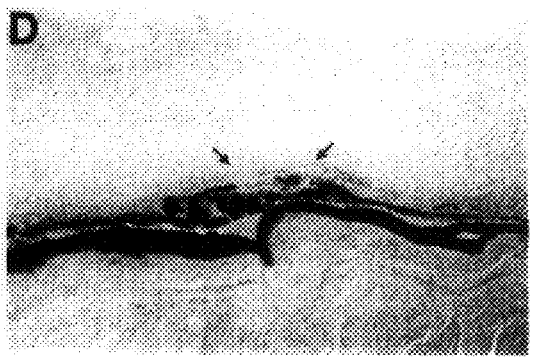
Figure 4E:
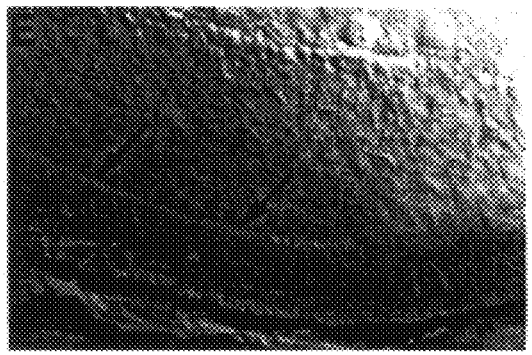

Immunohistochemical staining for VEGF in V-6+ mice showed reaction product within photoreceptors FIGS. 4A, C, and E). On some sections, there was diffuses staining of photoreceptor outer and inner segments (FIGS. 4A and E, arrows), but in general, the staining was quite focal, which is characteristic of expression driven by the bovine rhodopsin promoter fragment used in this study[30, 34]. When areas of NV and associated proliferation of the retinal pigmented epithelium were present, there was staining in adjacent photoreceptors (FIG. 4B, arrows), while unstained photoreceptors were often seen elsewhere on the section (arrowheads). However, since staining was also seen in some morphologically normal photoreceptors (FIGS. 4A and E), it is clear that the VEGF expression was not secondary to the morphologic changes. Preabsorption of primary antibody with antigenic peptide almost completely eliminated the staining (FIG. 4C, arrows). There was occasionally faint staining in the inner retina. This staining was also eliminated by preabsorption of primary antibody and probably represents endogenous VEGF expression.

EXAMPLE 6

Microscopic and Ultrastructural changes in the Retina

At several different time points and generally right after fluorescein angiography, mice were sacrificed, eyes were removed, and fixed in 4% glutaraldehyde in 0.1 M cacodylate buffer (pH 7.4) for 24 hours at 4° C. The anterior segments were removed from the eyes and under a dissecting microscope, areas corresponding to the sites of leakage on fluorescein angiography were dissected, postfixed with 1% osmium tetroxide/cacodylate buffer (pH 7.4), dehydrated through a series of graded alcohols, and embedded in Poly/Bed 812 resin (Polysciences, Warrington, Pa.). One micron sections were cut, stained with Toluidine Blue, and examined with an Axioscope microscope (Zeiss, Thornwood, N.Y.). For electron microscopy, ultrathin sections were cut, counterstained with 2.0% uranyl acetate and 0.3% lead citrate, and examined with a transmission electron microscope (JEOL 100CX).

V-6+ mice

At P7, transgene-positive (VEGF+) mice had normal-appearing retinas by light microscopy that showed no difference from littermate control mice. At P10, ectopic cells were seen in the outer nuclear layer (ONL) (FIG. 9 arrow) and at P14 similar cells were seen forming focal clusters (FIG. 9 arrow) .among outer segments adjacent to the RPE cell layer (arrowheads). Electron microscopy demonstrated tight junctions between these cells (FIG. 10A, inset) and no evidence of pigment granules. Electron microscopic immunocytochemical staining using monoclonal antibodies to a broad spectrum of keratin isotypes showed staining in the RPE layer, but the ectopic cells in the photoreceptor layer were negative (data not shown); however, the cells did stain with an endothelial cell-specific lectin (FIG. 11). By P18, some cell aggregates in the subretinal space (FIG. 9C, arrow) showed lumen formation (asterisk). The presence of red blood cells (FIG. 9C, left of asterisk; FIG. 10B) indicates that these cell clusters constitute a perfused blood vessel. By P21, well-formed blood vessels could be seen extending from the inner retina through the ONL into the outer segment layer (FIG. 9D). Electron microscopy showed neovascular complexes containing slit-like lumens (FIG. 10C, small arrows) in the ONL and in the subretinal space adjacent to the RPE. At P31, large blood vessels with adjacent multilayered colonies of RPE cells were seen among photoreceptor outer segments FIG. 9E). These blood vessels were partially surrounded by RPE cells (arrowheads) and were fenestrated (FIG. 10D, inset), although fenestrations were never seen in the portion of the vessels located in the ONL (not shown). At 6 weeks (P45) (FIG. 9F), large vessels from the inner retina connected to complex vascular networks in the subretinal space that were almost completely surrounded by RPE cells (arrowheads). FIG. 10E shows a region of a blood vessel in the subretinal space that is surrounded by RPE cells. A total of 76 eyes of VEGF+ mice between P7 and 4 months of age have been examined by various histologic techniques and blood vessels have never been seen extending from the choroid into the subretinal space.

V-24+ mice

At 4 days after birth there were no identifiable differences between V-24+ and V-24− mice, suggesting that photoreceptors develop normally in V-24+ mice. By 7 days there were beginning signs of photoreceptor degeneration in V-24+ mice (not shown). The photoreceptor degeneration progressed rapidly and by 14 days was widespread. In 3 month old mice, there were no normal-appearing photoreceptors and there was some disorganization of the inner nuclear layer (FIG. 6). Transgene-negative V-24 littermates had normal appearing retinas at all time points examined.

V-27+ mice

The retinas of five V-27+ mice were examined at 3–4 months after birth and were normal and therefore, no additional time points were examined.

EXAMPLE 7

Immunocytochemistry

Immunocytochemistry was performed on vibratome sections which were then flat-embedded between dimethyldichlorosilane (Sigma, St. Louis, Mo.) coated slides as previously described[49]. Briefly, eyes were fixed in a solution of 4% paraformaldehyde and 0.2% glutaraldehyde containing 8.5% sucrose and 1 nM $CaCl_2$ in phosphate buffer, pH 7.4, for 1 hour at room temperature and transferred to 4% paraformaldehyde with 1 mM $CaCl_2$ in 0.1 bicarbonate buffer, pH 10.4, in which they were incubated overnight at 4° C. The eyes were stored at 4° C. in phosphate-buffered saline, pH 7.4, containing 1 nM $CaCl_2$ until 50 $\mu$m sections were cut on a Lancer series 1000 vibratome (St. Louis, Mo.). Sections were incubated in a 1:250 dilution of mouse monoclonal antibodies to keratin from clones AE1 and AE3 (Hybritech, San Diego, Calif.) or a 1:20 dilution of Griffonia simplicifolia isolectin $B_4$ and stained as previously described[50, 51]. The diaminobenzidine-4HCl reacted sections were embedded in Poly/Bed 812 between dimethylchlorosilane-coated slides. After polymerization at 60° C., the resin was peeled from the slides and the sections were scanned by light microscopy under low power. Areas of interest were cut out and re-embedded in molds containing Poly/Bed 812. One micron sections were cut and used to identify areas of interest from which ultrathin sections were cut. Specimens were viewed with and without a uranyl acetate and lead citrate counterstain on a JEOL 100X electron microscope at 60 kV and photographed with 4489 electron microscope film (Kodak, Rochester, N.Y.).

EXAMPLE 8

Retinal Whole Mounts

In order to study the 3-dimensional architecture of the intraretinal and subretinal NV, VEGF+ mice were perfused with fluorescein-labeled dextran and retinal whole-mounts were prepared with the photoreceptor side up.

Mice were anesthetized with ether, the descending aorta was clamped, the right atrium was cut, and 1 ml of phosphate-buffered saline containing 50 mg/ml of fluorescein-labeled dextran ($2 \times 10^6$ average mw, Sigma, St. Louis, Mo.) was infused through the left ventricle as previously described by Smith et al.[48]. The eyes were removed and fixed for 1 hour in 10% phosphate-buffered formalin The cornea and lens were removed and the entire retina was carefully dissected from the eyecup, radially cut from the edge of the retina to the equator in all 4 quadrants, and flat-mounted in Aquamount with photoreceptors facing upward. Flat-mounts were examined by fluorescence microscopy and images were photographed, scanned, labeled, and printed as described above.

FIG. 12A shows the normal retinal vasculature of a P21 transgene-negative mouse. At low magnification, it is difficult to distinguish retinal NV in a P21 VEGF+ mouse (FIG. 12B), but at higher magnification focusing on the photoreceptor layer, numerous small foci of NV are visible with out-of-focus retinal blood vessels in the background (FIG. 12C). At even higher magnification (FIG. 12D), connecting vessels (often two, white arrowheads) can be seen between retinal vessels and the NV (black arrows). Many of the NV foci are partially surrounded by RPE cells (black arrowheads), as was noted in retinal sections. This same picture of numerous small foci of NV in the photoreceptor layer arising from vessels of the inner retina was seen in several other P21 VEGF+ mice (not shown). In P31 VEGF+ mice, less numerous but larger foci of NV more completely surrounded by RPE were seen (FIG. 12E, arrows). At 6 weeks of age, VEGF+ mice showed large fronds of looping NV in the photoreceptor layer (FIG. 12F, arrows).

Earlier time points were also examined and at P14 small abnormal blood vessels were seen extending beyond the plane of focus of the deep retinal capillary bed (FIG. 12G, arrow), but they did not extend all the way to the outer edge of the retina, as was the case in P21 mice. FIG. 13A–F shows six optical sections through the outer retina of a P14 mouse at 2.5 µm intervals obtained by scanning laser confocal microscopy; two NV buds (arrows) are traced back to their sites of origin in the deep capillary bed (E and F). At P18, small blood vessels (FIG. 12H, arrows) with adjacent clumps of RPE cells (arrowheads) were seen at the outer edge of the retina.

Quantitation of Retinal NV on Retinal Whole-mounts

Retinal whole-mounts were examined by fluorescence microscopy at 400x magnification, which provides a narrow depth of field so that when focusing on NV at the outer edge of the retina the remainder of the retinal vessels are out-of-focus, thus allowing easy delineation of the NV. The outer edge of the retina, which corresponds to the subretinal space in vivo, is easily identified and therefore there is standardization of focal plane from slide to slide. Images were digitized using a 3 CCD color video camera (IK-TU40A, Toshiba, Tokyo, Japan) and a frame grabber. Image-Pro Plus software (Media Cybernetics, Silver Spring, Md.) was used to delineate each of the lesions and calculate the number in each retina, the area of each lesion, and the total area of neovascularization per retina. Measurements were repeated three times for each retina and the mean was used for one experimental value; there was little variability among triplicate measurements. Whole mounts of mice from P14 through P18 were examined with a scanning laser confocal microscope (Bio-Rad MRC-600). Excitation wavelength was 488 nm and emission wavelength was 520–580nm. Horizontal optical sections (0.5 m–1.0 m) were obtained through the outer retina and captured and processed using COMOS version 6.03 (Bio-Rad).

Image analysis was used to count the number and calculate the area of NV lesions in the photoreceptor layer of VEGF+ mice at several time points (Table). On P14, no blood vessels were present at the outer edge of the retina, but by P18 many small lesions were seen. The number of lesions per retina, the area per lesion, and the total area of NV per retina all increased between P14 and P18. Between P18 and P21, the number of lesions per retina decreased, but the area per lesion and the total area of NV per retina increased. These data are consistent with our impression obtained from studying many flat-mounts at several -different time points, that there is some growth and coalescence of lesions over time (at least through 6 weeks) resulting in fewer, larger individual lesions and an increase in the total amount of NV.

TABLE

Quantitation of Neovascularization (NV) in the Photoreceptor Layer of VEGF Transgenic Mice

| Age (days) | N | Lesions/retina | Area/lesion ($mm^2 \times 10^{-3}$) | NV Area/retina ($mm^2 \times 10^{-3}$) |
|---|---|---|---|---|
| 14 | 10 | 0 | — | 0 |
| 18 | 6 | 27.0 ± 6.5 | 0.29 ± 0.03 | 8.39 ± 2.46 |
| 21 | 10 | 68.2 ± 13.2 | 0.46 ± 0.06 | 34.61 ± 7.56 |
| 31 | 10 | 42.1 ± 11.8 | 1.68 ± 0.06 | 52.67 ± 15.2 |
| 45 | 10 | 25.1 ± 8.6 | 4.49 ± 0.74 | 123. ± 54. |

P = 0.0002 by ANOVA for an age-related difference in the number of lesions
P = 0.0015 by ANOVA for an age-related difference in the area/lesion
P = 0.0223 by ANOVA for an age-related difference in the total area of NV/retina

Discussion

Several studies have demonstrated temporal and spatial correlation of VEGF expression with retinal NV[9-11]. However, attempts to determine if increased levels of VEGF alone are sufficient to cause retinal NV have been equivocal. With one exception in rabbit[23], it has not been possible to generate retinal NV by intraocular administration of VEGF. In addition, interpretation of such results is complicated by the fact that intraocular administration of exogenous VEGF necessarily involves some surgical trauma, which has been demonstrated to increase expression of basic FGF, another angiogenic growth factor, even in retinal cells remote from the trauma 31. In the present study, we used a transgenic approach to produced mice with increased expression of endogenous VEGF in the retina without the complication of surgical trauma. Three lines of mice that incorporated the rhodopsin promoter/VEGF transgene were generated and characterized. One line (V-27), which did not show expression of VEGF above baseline level, did not demonstrate a detectable phenotype. A second line (V-24), which exhibited transgene expression beginning approximately on day 7, demonstrated rapid and specific photoreceptor degeneration. The cause of the degeneration is presently unclear. One possibility is insertional mutagenesis caused by integration of the transgene into an essential retinal gene. If this is the case, the finding that animals heterozygous for the transgene display retinal degeneration implies haploinsufficiency of the affected gene is sufficient to cause photoreceptors cell loss. A second possibility is that, due to either altered time course or level of expression, VEGF itself is responsible for the loss of photoreceptors in the V-24+ mice. Arguing against this possibility, however, is that the transgene expression pattern is focal while the degeneration is rapid and diffuse. In any case, the V-24 line provides a new model of retinal degeneration and future studies are necessary to explore its molecular basis. The third line of transgenic mice (V-6) demonstrated sustained increased expression of VEGF in the retina and developed intraretinal and subretinal NV. The NV was more focal and limited than that seen in ischemic retinopathies. This may be due in part to the focal pattern of expression driven by the bovine rhodopsin promoter fragment[30, 34]. Another factor that may be important is the location of increased expression of VEGF within the retina; in V-6+ mice, VEGF expression is increased in the outer retina, while in ischemic retinopathies it is increased in the inner retina[9-11]. In addition, there is evidence suggesting that hypoxia, which is not part of the transgenic model, induces changes that may enhance the effects of VEGF, including induction of VEGF receptor expression[36] and death of astrocytes[26].

The nature of the NV caused by increased expression of VEGF in photoreceptors is interesting. It originates from the deep capillary bed located in the inner nuclear layer and extends down among photoreceptor outer segments and into the subretinal space, the site of the highest levels of VEGF. Despite its closer proximity, we were unable to detect any NV originating from the choroid. This indicates that high levels of VEGF in the outer retina are not sufficient to cause choroidal NV and supports our contention that angiogenic factors may not have the same effects in different vascular beds. However, although choroidal vessels do not contribute to the NV in our model, the NV does share two important characteristics with choroidal NV, its location and the response of the RPE. Choroidal NV starts in the sub-RPE space. It then spreads to the, subretinal space among photoreceptors, the location of the NV in our model. Possibly due in part to this location, choroidal NV is accompanied by proliferation of the RPE; in several models of choroidal NV, the RPE surrounds the NV, forms tight junctions, and re-establishes the blood-retinal barrier[37, 38], while in patients with age-related macular degeneration and choroidal NV, the RPE proliferates, but is incapable of re-establishing the barrier. In V-6+ mice, the RPE proliferates, but based upon the FA results in 4 month old mice, it does not appear able to re-establish the blood-retinal barrier. Therefore, although the NV in V-6+ mice originates from retinal blood vessels, it may also have implications for understanding some aspects of choroidal NV, the leading cause of severe vision loss in patients with age-related macular degeneration.

In addition to unequivocally demonstrating that increased expression of VEGF in the retina is sufficient to cause intraretinal and subretinal NV, the mice described in this report provide a useful model that has important advantages over previously described models of retinal NV for investigating the efficacy of potential angiogenesis inhibitors. Intravitreous injection of fibroblasts in rabbits causes retinal NV, but requires retinal detachment and unlike human retinal NV associated with ischemic retinopathies, inflammation plays a prominent role[39, 40]. Inflammation also plays a major role in trauma-induced retinal NV in rats[41]. Intravitreous injection of V-2 carcinoma cells in rabbits causes retinal NV without retinal detachment and with little evidence of inflammation, but the NV may take 100 days to develop[41], making the model impractical for testing antiangiogenic agents. Laser-induced retinal vein occlusion results in retinal ischemia, but rarely causes retinal NV in primates[43, 44] and the incidence of retinal NV in pigs[45] is sufficiently low (about 50%) to confound evaluation of drugs; an additional problem with these models is that they are prohibitively expensive.

Another group of models is based upon perturbation of retinal vascular development which is completed after birth in some species; placing neonates in a high oxygen environment inhibits development and promotes closure of retinal blood vessels. When returned to room air, the combination of lower inspired oxygen and a poorly developed retinal vasculature results in ischemic retinopathy and retinal NV. This approach has been used in dogs, cats, rats, and mice to establish models of retinal NV (for review see Patz, 1984)[46]; rodent models[47, 48] have been particularly useful because they are very reproducible and relatively inexpensive, but the NV regresses spontaneously over a fairly short time, which is a disadvantage. The model described in the present study complements the murine model of oxygen-induced ischemic retinopathy because it is not dependent on a particular developmental stage, which is a potentially important difference, and makes the model more analogous to diabetic retinopathy. Also, through at least four months, there is no spontaneous regression of the NV, making it possible to use the model to screen for pharmacologically-induced regression of NV, an important clinical goal.

REFERENCES

1. Kahn H, Hiller R: Blindness caused by diabetic retinopathy. Am J Ophthalmol 1974,78:58–67
2. Michaelson I: The mode of development of the vascular system of the retina with some observations on its significance for certain retinal diseases. Trans Ophthalmol Soc UK 1948,68:137–180
3. Ashton N: Retinal vascularization in health and disease. Am J Ophthalmol 1957,44(4):7–17
4. Shweiki D, Itin A, Soffer D, Keshet E: Vascular endothelial growth factor induced by hypoxia may mediate hypoxia-initiated angiogenesis. Nature 1992, 359:843–845
5. Plate K H, Breier G, Welch H A, Risau W: Vascular endothelial growth factor is a potential tumor angiogenesis factor in human gliomas in vivo. Nature 1992, 359:845–848
6. Adamis A P, Miller J W, Bernal M-T, D'Amico D J, Folkman J, Yeo T-K, Yeo K-T: Increased vascular endothelial growth factor levels in the vitreous of eyes with proliferative diabetic retinopathy. Am J Ophthalmol 1994, 118:445–450
7. Aiello L P, Avery R L, Arrigg P G, Keyt B A, Jampel H D, Shah S T, Pasquale L R, Thieme H, Iwamoto M A, Park J E, Nguyen M S, Aiello L M, Ferrara N, King G L: Vascular endothelial growth factor in ocular fluid of patients with diabetic retinopathy and other retinal disorders. N Engl J Med 1994,331:1480–1487
8. Malecaze F, Clamens S, Simorre-Pinatel V, Mathis A, Chollet P, Favard C, Bayard F, Plouet J: Detection of vascular endothelial growth factor messenger RNA and vascular endothelial growth factor-like activity in proliferative diabetic retinopathy. Arch Ophthalmol 1994, 112:1476–1482
9. Pe'er J, Shweiki D, Itin A, Hemo I, Gnessin H, Keshet E: Hypoxia-induced expression of vascular endothelial growth factor by retinal cells is a common factor in neovascularizing ocular diseases. Lab Invest 1995, 72:638–645
10. Miller J W, Adamis A P, Shima D T, D'Amore P A, Moulton R S, O'Reilly M S, Folkman J, Dvorak H F, Brown L F, Berse B, Yeo T-K, Yeo K-T: Vascular endothelial growth factor/vascular permeability factor is temporally and spatially correlated with ocular angiogenesis in a primate model. Am J Pathol 1994,145:574–584
11. Pierce E A, Avery R L, Foley E D, Aiello L P, Smith L E H: Vascular endothelial growth factor/vascular permeability factor expression in a mouse model of retinal neovascularization. Proc Natl Acad Sci USA 1995, 92:905–909
12. Aiello L P, Pierce E A, Foley E D, Takagi H, Chen H. Riddle L, Ferrara N, King G L, Smith L E H: Suppression of retinal neovascularization in vivo by inhibition of vascular endothelial growth factor (VEGF) using soluble VEGF-receptor chimeric proteins. Proc Natl Acad Sci USA 1995,92:10457–10461
13. Robinson G S, Pierce E A, Rook S L, Foley E, Webb R, Smith L E S: Oligodeoxynucleotides inhibit retinal neovascularization in a murine model of proliferative retinopathy. Proc Natl Acad Sci USA 1996,93:4851–4856
14. Adamis A P, Shima D T, Tolentino M J, Gragoudas E S, Ferrara N, Folkman J, D'Amore P A, Miller J W: Inhibition of vascular endothelial growth factor prevents 14. retinal ischemia-associated iris neovascularization. Arch Ophthalmol 1996,114:66–71
15. Leung D W, Cachianes G, Kuang W-J, Goeddel D V, Ferrara N: Vascular endothelial growth factor is a secreted angiogenic mitogen. Science 1989,246:1306–1309
16. Connolly D T, Heuvelman D M, Nelson R, Olander J V, Eppley B L, Delfino J J, Siegal N R, Leimgruber R M, Feder J: Tumor vascular permeability factor stimulates endothelial cell growth and angiogenesis. J Clin Invest 1989,84:1470–1478
17. Flamme I, von Reutern M, Drexler H C A, Sarwar S-A, Risau W: Overexpression of vascular endothelial growth factor in the avian embryo induces hypervascularization and increased vascular permeability without alterations of embryonic pattern formation. Devel Biol 1995, 171:399–414
18. Takeshita S, Tsurumi Y, Couffinahl T, Asahara T, Bauters C, Symes J, Ferrara n, Isner J M: Gene transfer of naked DNA encoding for three isoforms of vascular endothelial growth factor stimulates collateral development in vivo. Lab Invest 1996,75:487–501
19. Lutty G A, McLeod S D, Merges C, Diggs A, Plouet J: Localization of vascular endothelial growth factor in human retina and choroid. Arch Opthalmol 1996, 114:971–977
20. Vinores S A, Youssri A I, Luna J D, Chen Y-S, Bhargave S, Vinores M A, Schoenfeld C-L, Peng B, Chan C C, LaRochelle W, Green W R, Campochiaro P A: Upregulation of vascular endothelial growth factor in ischemic and non-ischemic human and experimental retinal disease. Histol Histopathol 1996, In press
21. Tolentino M J, Miller J W, Gragoudas E S, Chatzistefanou K, Ferrara N, Adamis A P: Vascular endothelial growth factor is sufficient to produce iris neovascularization and neovascular glaucoma in a nonhuman primate. Arch Ophthalmol 1996,114:964–970
22. Tolentino M J, Miller J W, Gragoudas E S, Jakobiec F A, Flynn E, Chatzistefanou K, Ferrara N, Adamis A P: Intravitreous injections of vascular endothelial growth factor produce retinal ischemia and microangiopathy in an adult primate. Ophthalmology 1996,103:1820–1828
23. Ozaki H Hayashi H Vinores S A, Moromisato Y, Campochiaro P A, Oshima K: Intravitreal sustained release of VEGF causes retinal neovascularization in rabbits and breakdown of the blood-retinal barrier in rabbits and primates. Exp Eye Res 1996, In press
24. Kim S I, Ng E W M, Kenney A G, Tolentino M J, Connolly E J, Gragoudas E S, Miller J W: Rat model of subretinal choroidal neovascular membrane formation. Invest Ophthalmol Vis Sci 1996,37: S125
25. Janzer R C, Raff M C: Astrocytes induce blood-brain barrier properties in endothelial cells. Nature 1987, 325:253–257
26. Stone J, Chan-Ling T, Pe'er J, Itin A, Gnessin H, Keshet E: Roles of vascular endothelial growth factor and astrocyte degeneration in the genesis of retinopathy of prematurity. Invest Opthalmol Vis Sci 1996,37:290–299
27. Frank R N, Turczyn T J, Das A: Pericyte coverage of retinal and cerebral capillaries. Invest Ophthalmol Vis Sci 1990,31:999–1007
28. Orlidge A, D'Amore P A: Inhibition of capillary endothelial cell growth by pericytes and smooth muscle cells. J Cell Biol 1987,105:1455–1462
29. Dellian M, Witwer B P, Salehi H A, Yuan F, Jain R K: Quantitation and physiological characterization of angiogenic vessels in mice. Effect of basic fibroblast growth factor, vascular endothelial growth factor/vascular permeability factor, and host microenvironment. Am J Pathol 1996,149:59–71
30. Zack D J, Bennett J, Wang Y, Davenport C, Klaunberg B, Gearhart J, Nathans J: Unusual topography of bovine rhodopsin promoter-lac z fusion gene expression in transgenic mouse retinas. Neuron 1991,6:187–199
31. Chomczynski P, Sacchi N: Single-step method of RNA isolation by acid guanidinium thiocyanate-phenol-chloroform extraction. Anal Biochem 1987,162:156–159
32. Campochiaro P A, Hackett S F, Vinores S A, Freund J, Csaky C, La Rochelle W, Henderer J, Johnson M, Rodriguez I R, Friedman Z. Dervjanik N, Dooner J: Platelet-derived growth factor is an autocrine growth stimulator in retinal pigmented epithelial cells. J Cell Sci 1994, 107:2459–2469
33. Breier G, Albrecht U, Sterrer S, Risau W: Expression of vascular endothelial growth factor during embryonic angiogenesis and endothelial cell differentiation. Development 1992,114C521–532):521–532
34. Campochiaro P A, Chang M, Ohsato M, Vinores S A, Nie Z, Hjelmeland L, Mansukhani A, Basilico C, Zack D J: Retinal degeneration in transgenic mice with photoreceptor-specific expression of a dominant-negative fibroblast growth factor receptor. J Neurosci 1996, 16:1670–1688
35. Wen R, Song Y, Cheng T, Matthes M T, Yasumura D, LaVail M M, Steinberg R H: Injury-induced upregulation of bFGF and CNTF mRNAs in the rat retina. J Neurosci 1995,15:7377–7385
36. Brogi E, Schatteman G, Wu T, Kim E A, Varticovski L, Keyt B, Isner J M: Hypoxia-induced paracrine regulation of vascular endothelial growth factor receptor expression. J Clin Invest 1996,97:469–476
37. Miller I, Miller B, Ryan S J: The role of the retinal pigmented epithelium in the involution of subretinal neovascularization. Invest Ophthalmol Vis Sci 1986, 27:1644–1652
38. Tobe T, Takahashi K, Ohkuma H. Uyama M: Experimental choroidal neovascularization in the rat. J Jap Ophthalmol Soc 1994,98:837–845
39. Tano Y, Chandler D, Machemer R: Retinal neovascularization after intravitreal fibroblast injection. Am J Ophthalmol 1981,92:103–109
40. Antoszyk A, Gottlieb J, Machemer R, Hatchell D: The effects of intravitreal triamcinolone acetonide on experimental pre-retinal neovascularization. Graefe's Arch Clin Exp Opthalmol 1993,231:34–40
41. Murata T, Ishibashi T, Inomata H: Experimental rat model of NV arising from the optic disk. Ophthalmic Res 1993,25:157–161
42. Finkelstein D, Bren S, Patz A, Folkman J, Miller S, HoChen C: Experimental retinal neovascularization induced by intravitreal tumors. Am J Ophthalmol 1977, 83:660–664
43. Miller J W, Stinson W, Folkman J: Regression of experimental iris neovascularization with systemic alpha-interferon. Ophthalmology 1993,100:9–14
44. Virdi P, Hayreh S: Ocular neovascularization with retinal vascular occlusion. I. Association with retinal vein occlusion. Arch Ophthalmol 1980,100:331–341
45. Pournaras C, Tsacopoulos M, Strommer K, Gilodi N, Leuenberger P M: Experimental retinal branch vein occlusion in miniature pigs induces local tissue hypoxia and vasoproliferative microangiopathy. Ophthalmology 1990, 97:1321–1328
46. Patz A: Current concepts of the effect of oxygen on the developing retina. Curr Eye Res 1984,3:159–163

47. Penn J S, Tolman B L, Lowery L A: Variable oxygen exposure causes preretinal neovascularization in the newborn rat. Invest Ophthalmol Vis Sci 1993,34:576–585
48. Smith L E H Wesolowski E, McLellan A, Kostyk S K, D'Amato R, Sullivan R, D'Amore P A: Oxygen-induced retinopathy in the mouse. Invest Ophthalmol Vis Sci 1994,35:101–111
49. Vinores S A, Herman M M, Rubinstein L J, Marangos P J. Electron microscopic localization of neuron-specific enolase in rat and mouse brain. *J Histochem Cytochem.* 1984;32: 1295–1302.
50. Vinores S A, Campochiaro P A, McGehee R, Orman W, Hackett S F, Hjelmeland L M. Ultrastructural and immunocytochemical changes in retinal pigment epithelium, retinal glia, and fibroblasts in vitreous culture. *Invest Ophthalmol Vis Sci.* 1990;3 1:2529–2545.
51. Luna J, Tobe T, Mousa S A, Reilly T M, Campochiaro P A. Antagonists of integrin alpha-v beta-3 inhibit retinal neovascularization in a murine model. *Lab Invest.* 1996;75:563–573.

What is claimed is:

1. A transgenic mouse whose genome comprises a polynucleotide encoding vascular endothelial growth factor (VEGF) under the transcriptional control of a bovine rhodopsin promoter, wherein said transgenic mouse has increased VEGF expression in the retina as compared to a wild-type mouse, and wherein said increased VEGF expression causes increased vascularization of the retina or subretinal space of the transgenic mouse as compared to a wild-type mouse.

2. The transgenic mouse of claim 1 wherein the VEGF is a mammalian VEGF.

3. The transgenic mouse of claim 1 wherein the VEGF is human VEGF.

4. The transgenic mouse of claim 1 wherein the VEGF is bovine VEGF.

5. A method of screening test compounds as potential drugs for altering vascularization in the retina or subretinal space, comprising the steps of:

administering a test compound to a transgenic mouse whose genome comprises a polynucleotide encoding vascular endothelial growth factor (VEGF) under the transcriptional control of a bovine rhodopsin promoter, wherein said transgenic mouse has increased VEGF expression in the retina as compared to a wild-type mouse, and wherein said increased VEGF expression causes increased vascularization of the retina or subretinal space of the transgenic mouse as compared to a wild-type mouse; and determining the extent of vascularization in the retina or subretinal space of said transgenic mouse, wherein an alteration in said extent of vascularization, as compared to the extent of vascularization in the retina or subretinal space of an equivalent transgenic mouse which did not receive the test compound, indicates the test compound is a potential drug for altering vascularization in the retina or subretinal space.

6. The method of claim 5 wherein the step of determining lesions employs light microscopy.

7. The method of claim 5 wherein the step of determining lesions employs immunostaining.

8. The method of claim 5 wherein the step of determining lesions employs electron microscopy.

9. The method of claim 5 wherein the step of determining lesions employs retinal whole mounts.

10. The method of claim 5 wherein the step of determining lesions employs retinalflat mounts.

11. The method of claim 5 wherein the step of administering is performed prior to postnatal day 6.

12. The method of claim 5 wherein the step of administering is performed prior to postnatal day 10.

13. A method of screening test therapies as potential therapies for altering vascularization in the retina or subretinal space, comprising the steps of:

administering a test therapy to a transgenic mouse whose genome comprises a polynucleotide encoding vascular endothelial growth factor (VEGF) under the transcriptional control of a bovine rhodopsin promoter, wherein said transgenic mouse has increased VEGF expression in the retina as compared to a wild-type mouse, and wherein said increased VEGF expression causes increased vascularization of the retina or subretinal space of the transgenic mouse as compared to a wild-type mouse; and determining the extent of vascularization in the retina or subretinal space of said transgenic mouse, wherein an alteration in said extent of vascularization, as compared to the extent of vascularization in the retina or subretinal space of an equivalent transgenic mouse which did not receive the test therapy, indicates the test therapy is a potential therapy for altering vascularization in the retina or subretinal space.

14. The method of claim 13 wherein the test therapy is a regime of radiation.

15. The method of claim 13 wherein the test therapy is a regime of photodynamic therapy.

16. The method of claim 13 wherein the test therapy is a regime of gene therapy.

* * * * *